United States Patent [19]

Cadogan et al.

[11] 4,440,676

[45] Apr. 3, 1984

[54] PROCESS FOR THE PRODUCTION OF A DIPEPTIDE, A POLYPEPTIDE OR A PROTEIN

[75] Inventors: John I. G. Cadogan, Richmond, England; Ian Gosney; Salih Yaslak, both of Edinburgh, Scotland

[73] Assignee: The British Petroleum Company p.l.c., London, England

[21] Appl. No.: 381,781

[22] Filed: May 25, 1982

[30] Foreign Application Priority Data

Dec. 24, 1981 [GB] United Kingdom ................ 8138996

[51] Int. Cl.$^3$ ........................................... C07C 103/52
[52] U.S. Cl. ............................................. 260/112.5 R
[58] Field of Search ................................ 260/112.5 R

[56] References Cited

PUBLICATIONS

Cadogan, et al., J. Chem. Soc. Chem. Commun., (1982), 298–299.

Primary Examiner—Delbert R. Phillips
Attorney, Agent, or Firm—Brooks, Haidt, Haffner & Dellahunty

[57] ABSTRACT

The invention lies in the field of peptide and protein synthesis. It related to the use of pentaco-ordinate phosphoranes, such as 2-hydro-2,2'-spirobis(1,3,2-benzodioxaphosphole) as coupling agents in a process for the production of a dipeptide, a polypeptide or a protein. Coupling is preferably effected in the presence of both a tertiary amine and a solvent and advantageously in the additional presence of an oxazalone formation suppressant, such as N-hydroxysuccinimide.

10 Claims, No Drawings

PROCESS FOR THE PRODUCTION OF A DIPEPTIDE, A POLYPEPTIDE OR A PROTEIN

The present invention relates generally to peptide linkages, as found in dipeptides, polypeptides and proteins, and in particular to the use of pentaco-ordinate phosphoranes, such as 2-hydro-2,2'-spirobis(1,3,2benzodioxaphosphole), as coupling agents in the formation of peptide linkages.

Peptide linkages are formed by condensation of the carboxyl group of one amino-acid with the amino group of the same or a different amino-acid and are characterised as the —CONH— group. A single peptide linkage is present in a dipeptide, a plurality of peptide linkages in a polypeptide and a vast number of peptide linkages in a protein, which may be regarded as a polymeric polypeptide. The general principle of peptide synthesis may be illustrated by consideration of the synthesis of a dipeptide. Two different amino-acids $H_2N—A—COOH$ and $H_2N—B—COOH$, may be combined in two different ways to form:

$$H_2NACONHBCOOH \quad H_2NBCONHACOOH$$
$$(I) \quad\quad\quad (II)$$

To prepare (I), the amino group of A must be protected and the carboxyl group of A must be activated so that it readily reacts with the free amino-group of B. Similarly to prepare (II), the amino-group of B must be protected and the carboxyl group of B must be activated. Hence, if Y is the protecting group and Z is the activating group the synthesis of (I) and (II) may be as follows:

(I)$H_2NACOOH \xrightarrow{Y} YNHACOOH \xrightarrow{Z}$

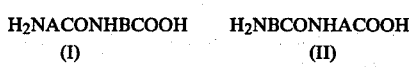

$YNHACOZ \xrightarrow{H_2NBCOOH} YNHACONHBCOOH$

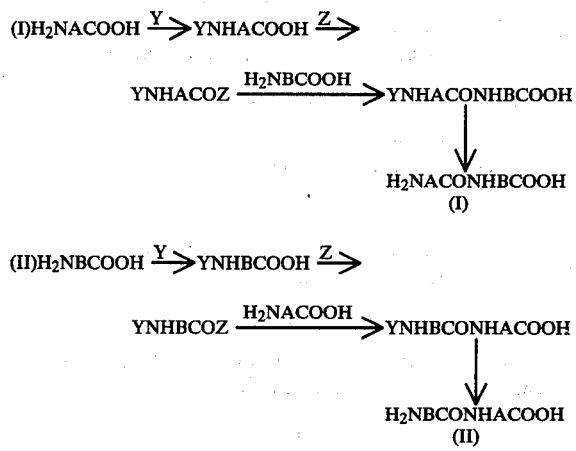

In each case, the final step involves the removal of the protecting group Y to give the dipeptide. Alternatively, the amino-group of the amino-acid which is to be N-terminal is protected and so is the carboxyl group of the amino-acid which is to be C-terminal. These two protected amino-acids may then be combined directly by means of a coupling agent to give a dipeptide protected at both its N- and C-terminals. Thus (I) may be synthesised as follows (R is the carboxyl protecting group):

$YNHACOOH +$

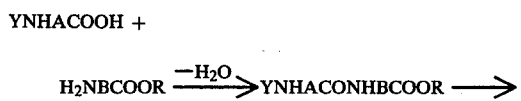

In a further alternative, the carboxyl group of the N-terminal protected amino-acid may be converted into an activated group and, after combination of the two amino-acid derivatives, a dipeptide is obtained which again has both its N- and C-terminals protected, eg the synthesis of (II):

$YNHBCOZ + H_2NACOOR \longrightarrow YNHBCONHACOOR \longrightarrow$

To extend the length of the peptide chain, one of the protecting groups in the protected dipeptide is selectively removed and the peptide is built up from this end. Thus, a peptide chain may be extended, one amino-acid residue at a time, from either end of its precursor. On the other hand, a number of suitable simple peptides may be synthesised and these then linked together to give the required protected peptide (or protein), from which the protecting groups are finally removed. Furthermore, if the amino-acid has a side-chain containing reactive groups, these must be protected. The present invention is not concerned with protecting groups, but in the means, ie the coupling agent, employed to effect the direct combination between an end aminogroup and an end carboxyl group. An important property of a coupling agent is that it should not lead to any rearrangement or racemisation of the reactants during the coupling.

Over the years a variety of coupling agents has been employed. These include isobutyl chloroformate, dicyclohexylcarbodi-imide (DCC), N-ethyl-5-phenylisoxazolium-3'-sulphonate (NEPIS) and N-ethoxycarbonyl-2-ethoxy-1,2-dihydroquinoline (EEDQ), sometimes in combination with N-hydroxysuccinimide. Recently, several new coupling agents for peptide synthesis have been reported. Thus Bates et al in *Helvetica Chimica Acta*, 1975, 58, 688 and Galpin et al in *Tetrahedron*, 1976, 32, 2417 disclose the use of u-oxo-bis[tris-(dimethylamino)-phosponium]bis-tetrafluoroborate as a coupling agent which, in the presence of additives, gives less than 1% racemate. Wakselman in *J.C.S. Chemical Communications*, 1981, 632, discloses the use as a coupling agent of 5-nitro-3-H-1,2-benzoxathiole SS-dioxide. This coupling agent leads to less than 0.7% racemate.

It has now been found that pentaco-ordinate phosphoranes, eg 2-hydro-2,2'-spirobis(1,3,2-benzodioxaphosphole) are practical coupling agents in the formation of peptide linkages and furthermore, that their use in combination with certain bases, solvents and additives in peptide syntheses susceptible to racemisation can lead to less than 0.1% racemisation.

Accordingly the present invention provides a process for the production of a dipeptide, polypeptide or a protein wherein an end amino-group is directly combined with an end carboxyl group in the presence of a coupling agent to form a peptide linkage characterised in that the coupling agent is a pentaco-ordinate spirophosphorane.

The end amino-group may suitably be attached to a first aminoacid or polypeptide residue and the end carboxyl group attached to a second amino-acid or polypeptide residue, which first and second amino-acid or polypeptide residues may be the same or different. Any amino-acid residue may be used in the process of the invention. Suitable amino-acid residues include alpha and beta-alanine (Ala), aspartic acid (Asp), asparagine, arginine (Arg), cysteine (Cy-SH), cystine (Cy-S), glutamic acid (Glu), glutamine, glycine (Gly), histidine (His), leucine (Leu), isoleucine (Ilen), lysine (Lys), methionine (Met), ornithine, phenylalanine (Phe), proline (Pro), hydroxyproline (Hyp), serine (Ser), threonine (Thr), tryptophan (Try), tyrosine (Tyr) and valine (Val). Suitable polypeptide residues may contain one or more of the aforesaid aminoacid residues.

The coupling agent is a pentaco-ordinate spirophosphorane. A preferred coupling agent is 2-hydro-2,2'-spirobis(1,3,2-benzodioxaphosphole) of formula:

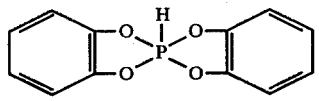 (A)

It is preferred to employ the coupling agent in conjunction with both a tertiary amine and a solvent. Particularly suitable solvents include tetrahydrofuran (THF) and dimethylformamide (DMF). Examples of suitable tertiary amines include triethylamine, N-methylmorpholine (NMM) and diethylaminomethylpolystyrol (DEAMP), of which diethylaminomethylpolystyrol is preferred. It is particularly preferred to add oxazalone formation suppressants, for example, N-hydroxysuccinimide (HOSu) in addition to the tertiary amine and the solvent.

The combination of the end amino-group with the end carboxyl group may be effected over a moderately wide temperature range, suitably in the range from 0° to 150° C., preferably from 15° to 60° C., and over a period suitably in the range from 12 hours to 20 days, preferably from 1 to 7 days. The pressure may suitably be atmospheric pressure.

The process of the invention will now be illustrated by reference to the following Examples in which Z—Gly—(L)Ala—OH is coupled with H—(L)Leu—OBzl and the product after hydrogenation is analysed, using an amino-acid analyser, for traces of Gly—(D,L)Ala—(L)Leu, according to a stringent racemisation test developed by N. Izumiya and M. Muraoka, as published in *J. Am. Chem. Soc.*, 1969, 91, 2391. The proposed sequence is:

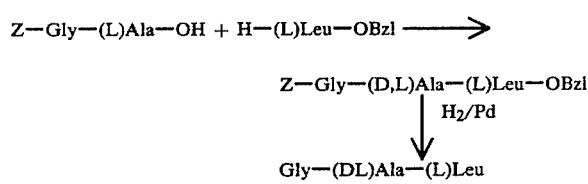

The extent of racemisation is defined as:

$$\frac{\{100[I(D,L)]\}}{\{[I(L,L)] + [I(D,L)]\}}$$

in which I=Gly—Ala—Leu.

EXAMPLE 1

To a stirred solution (dry THF) of 0.5 mmol Z—Gly—(L)Ala—OH and 1 mmol 2-hydro-2,2'-spirobis(1,3,2-benzodioxaphosphole) in 5 ml dry THF was added a mixture of the p-toluenesulphonate of H—(L)Leu—OBzl and triethylamine (0.5 mmol each in 5 ml dry THF). The mixture was held at 20° C. for 14 days, after which the solvent was evaporated off. After addition of 10 ml ethyl acetate the peptide was treated with sodium bicarbonate and dilute hydrochloric acid. The ethyl acetate layer gave Z—Gly—(D,L)Ala—(L)Leu—OBzl which was hydrogenated to yield Gly—(DL)Ala—(L)Leu. This was analysed using a Beckman 120C automatic amino-acid analyser. The results are given in the Table.

EXAMPLE 2

The procedure of Example 1 was repeated except that the temperature was 60° C. and the reaction time was 1 day.

EXAMPLE 3

The procedure of Example 1 was repeated except that the temperature was 100° C. and the reaction time was 1 day.

EXAMPLE 4

The procedure of Example 1 was repeated except that the triethylamine was replaced by NMM, the temperature was 60° C. and the reaction time was 7 days.

EXAMPLE 5

The procedure of Example 4 was repeated except that the temperature was 40° C.

EXAMPLE 6

The procedure of Example 5 was repeated except that the reaction time was 4 days.

EXAMPLE 7

The procedure of Example 6 was repeated using DMF as solvent in place of THF.

EXAMPLE 8

The procedure of Example 6 was repeated except that HOSu (3 mmol) were added to the mixture.

EXAMPLE 9

The procedure of Example 6 was repeated except that NMM was replaced by DEAMP.

EXAMPLE 10

The procedure of Example 9 was repeated except that the temperature was 18° C. and the reaction time was 7 days.

EXAMPLE 11

The procedure of Example 9 was repeated except that HOSu (3 mmol) was added to the mixture.

EXAMPLE 12

The procedure of Example 11 was repeated except that the temperature was 25° C.

EXAMPLE 13

The procedure of Example 12 was repeated except that the reaction time was 2 days.

EXAMPLE 14

The procedure of Example 12 was repeated except that the reaction time was 1 day.

EXAMPLE 15

The procedure of Example 11 was repeated except that the temperature was 18° C. and the reaction time was 7 days.

The results of Examples 2 to 15 are given in the following Table.

TABLE

| Ex. | Base | Solvent | Additive | Temp (°C.) | Time (days) | Yield (%) | Extent of racemisation (%) |
|-----|------|---------|----------|------------|-------------|-----------|---------------------------|
| 1 | Et$_3$N | THF | — | 20 | 14 | 30 | 18 |
| 2 | Et$_3$N | THF | — | 60 | 1 | 50–60 | 20 |
| 3 | Et$_3$N | THF | — | 100 | 1 | 50–60 | 23 |
| 4 | NMM | THF | — | 60 | 7 | 50–60 | 21 |
| 5 | NMM | THF | — | 40 | 7 | 50–60 | 12 |
| 6 | NMM | THF | — | 40 | 4 | 50–60 | 11 |
| 7 | NMM | DMF | — | 40 | 4 | 50–60 | 11.3 |
| 8 | NMM | THF | HOSu | 40 | 4 | 60 | 4.1 |
| 9 | DEAMP | THF | — | 40 | 4 | 65 | 3.2 |
| 10 | DEAMP | THF | — | 18 | 7 | 40 | 1.3 |
| 11 | DEAMP | THF | HOSu | 40 | 4 | 65 | less than 0.1 |
| 12 | DEAMP | THF | HOSu | 25 | 4 | 65 | less than 0.1 |
| 13 | DEAMP | THF | HOSu | 25 | 2 | 60 | less than 0.1 |
| 14 | DEAMP | THF | HOSu | 25 | 1 | 60 | less than 0.1 |
| 15 | DEAMP | THF | HOSu | 18 | 7 | 40 | less than 0.1 |

We claim:

1. In a process for the production of a dipeptide, a polypeptide or a protein wherein an end amino-group is directly combined with an end carboxyl group in the presence of a coupling agent to form a peptide linkage the improvement which comprises using as the coupling agent a pentaco-ordinate spirophosphorane.

2. A process according to claim 1 wherein the coupling agent is 2-hydro-2,2'-spirobis(1,3,2-benzodioxaphosphole).

3. A process according to either claim 1 or claim 2 wherein the coupling agent is employed in conjunction with both a tertiary amine and a solvent.

4. A process according to claim 1 or claim 2 wherein the coupling agent is employed in conjunction with both a tertiary amine selected from triethylamine, N-methylmorpholine and diethylaminomethylpolystyrol and a solvent selected from tetrahydrofuran and dimethylformamide.

5. A process according to claim 4 wherein the tertiary amine is diethylaminomethylpolystyrol.

6. A process according to claim 1 wherein there is added an oxazalone formation suppressant.

7. A process according to claim 6 wherein the oxazalone formation suppressant is N-hydroxysuccinimide.

8. A process according to claim 1 wherein the end amino-group is attached to a first amino-acid or polypeptide residue and the end carboxyl group is attached to a second amino-acid or polypeptide residue, which first and second amino-acid or polypeptide residues may be the same or different.

9. A process according to claim 1 wherein the combination of the end amino-group with the end carboxyl group is effected at a temperature in the range from 0° to 150° C. over a period of from 12 hours to 20 days.

10. A process according to claim 1 wherein the combination of the end amino-group with the end carboxyl group is effected at a temperature in the range from 15° to 60° C. over a period of from 1 to 7 days.

* * * * *